United States Patent
Björling

(10) Patent No.: US 6,745,075 B2
(45) Date of Patent: Jun. 1, 2004

(54) METHOD AND APPARATUS FOR DETECTION OF PREMATURE ATRIAL CONTRACTION

(75) Inventor: Anders Björling, Järfälla (SE)

(73) Assignee: St. Jude Medical AB, Järfälla (SE)

( * ) Notice: Subject to any disclaimer, the term of this patent is extended or adjusted under 35 U.S.C. 154(b) by 337 days.

(21) Appl. No.: 10/027,156

(22) Filed: Dec. 20, 2001

(65) Prior Publication Data

US 2003/0120165 A1 Jun. 26, 2003

(51) Int. Cl.$^7$ ............................................. A61N 1/362
(52) U.S. Cl. ............................. 607/9; 600/509; 600/374
(58) Field of Search ............................. 600/374, 375, 600/508, 509, 515; 607/122, 126

(56) References Cited

U.S. PATENT DOCUMENTS

| | | | |
|---|---|---|---|
| 5,306,292 A | | 4/1994 | Lindegren ..................... 607/11 |
| 5,388,578 A | * | 2/1995 | Yomtov et al. ............. 600/375 |
| 6,266,554 B1 | | 7/2001 | Hsu et al. .................... 600/515 |
| 6,308,095 B1 | | 10/2001 | Hsu et al. .................... 600/518 |
| 2002/0091330 A1 | * | 7/2002 | MacAdam et al. ......... 600/509 |

\* cited by examiner

*Primary Examiner*—Carl Layno
(74) *Attorney, Agent, or Firm*—Schiff Hardin LLP

(57) ABSTRACT

In a method for identifying and classifying premature atrial contractions, a cardiac lead having multiple electrodes, electrically separated from each other, at its tip is placed in contact with cardiac tissue, so that at least two of the electrodes are simultaneously in contact with the cardiac tissue. When a depolarization wave arrives at the tip, respective unipolar signals are detected from multiple electrodes in contact with the cardiac tissue, and these signals are analyzed, such as by identifying a time offset between pairs of the signals, to identify a propagation direction of the depolarization wave. Dependent on this propagation direction, the depolarization wave is classified as representing a normal sinus beat or a premature atrial contraction. By further analysis, the premature atrial contraction, if present, is classified as originating either from the right atrium or the left atrium.

33 Claims, 4 Drawing Sheets

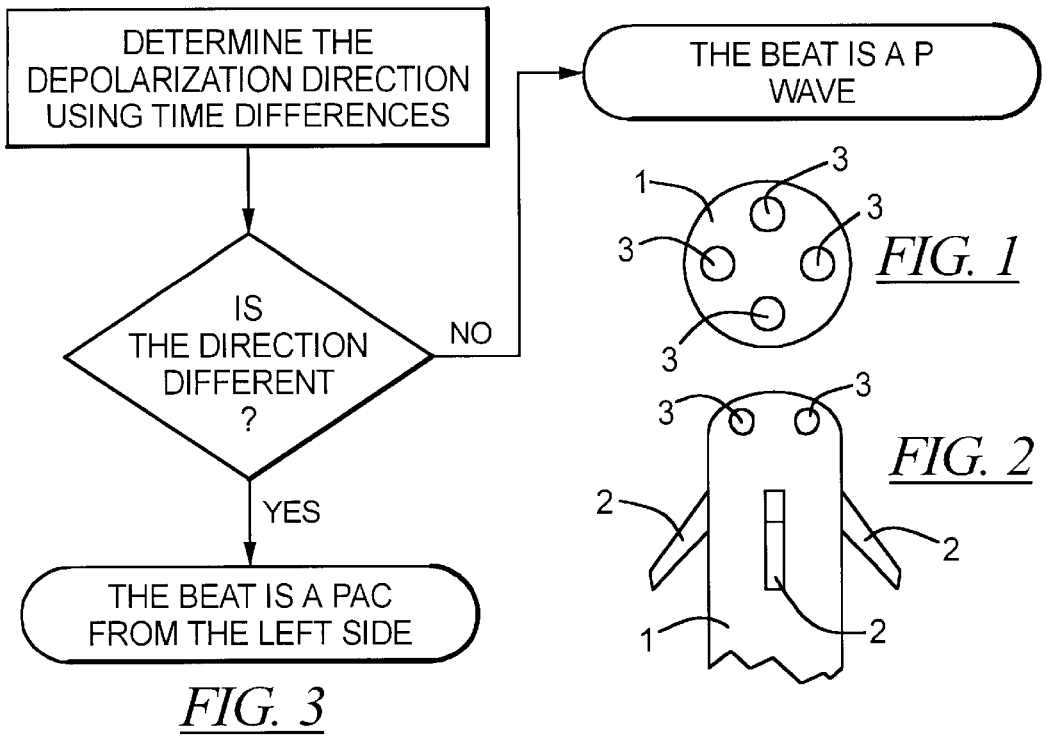
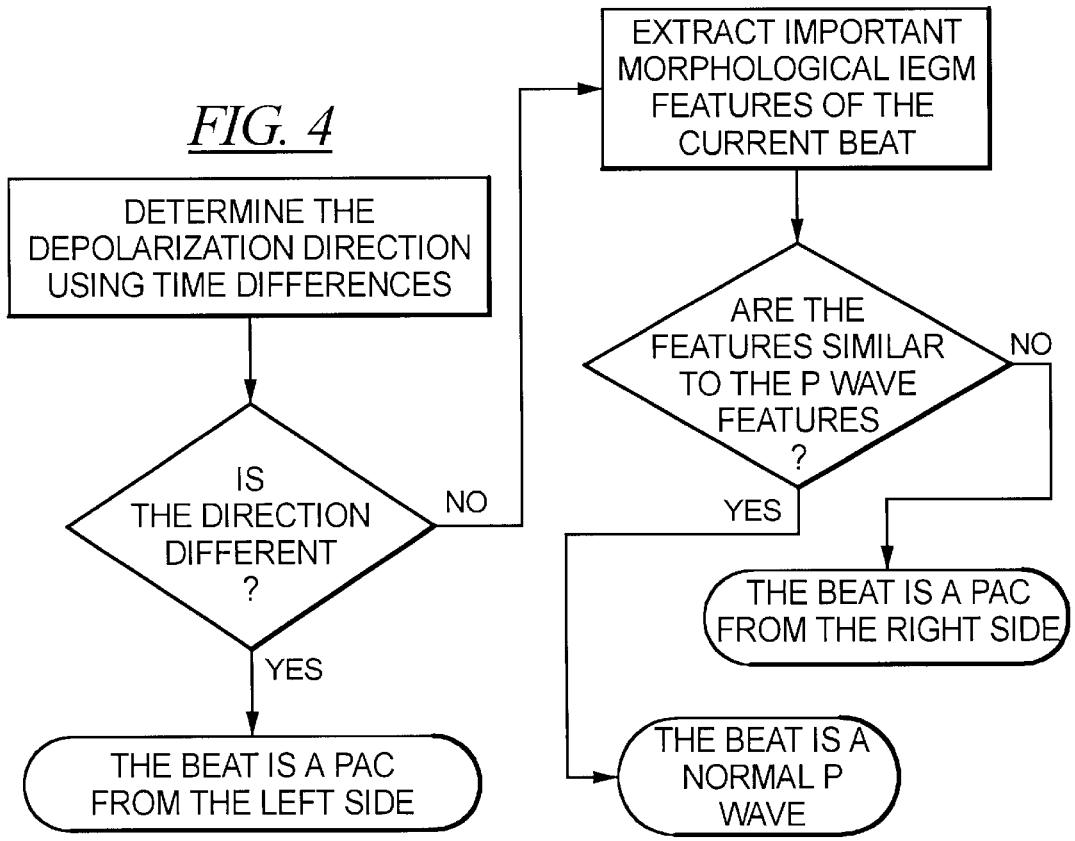

METHOD AND APPARATUS FOR DETECTION OF PREMATURE ATRIAL CONTRACTION

RELATED APPLICATIONS

The subject matter of the present application is related to the subject matter of United States application entitled "Method And Circuit For Detecting Cardiac Rhythm Abnormalities by Analyzing Time Differences Between Unipolar Signals From a Lead With a Multi-Electrode Tip," Björling et al. (Ser. No. 09/995,198, filed Nov. 27, 2001) and United States application entitled "Method and Circuit for Detecting Cardiac Rhythm Abnormalities Using a Differential Signal from a Lead with a Multi-Electrode Tip," Hedberg (Ser. No. 09/999,131, filed Nov. 30, 2001). The teachings of both of these applications are incorporated herein by reference.

BACKGROUND OF THE INVENTION

1. Field of the Invention

The present invention is directed to a method and an apparatus for detecting premature atrial contraction (PAC), and in particular to such a method and apparatus employing a cardiac lead having a multi-electrode tip.

2. Description of the Prior Art

Analysis of signal morphology, and time offsets between recurring features of an IEGM signal, for the purpose of classifying the signal as representing a particular type of cardiac activity, are known from U.S. Pat. No. 6,308,095 and U.S. Pat. No. 6,266,554. In the known techniques described in these patents, either a single signal is analyzed as it is received over time, or multiple signals, respectively received from relatively widely spaced apart electrodes, are analyzed. Since the electrodes are spatially separated, the propagating wavefront arising due to cardiac electrical activity will completely pass a first of the electrodes in its propagation path before reaching subsequent electrodes in its propagation path. In the intervening propagation distance between the spaced apart electrodes, the signals may be corrupted by noise, and it may further be difficult to determine whether the "same" signal is being received at the subsequent electrode as was "seen" by the first electrode. This makes it difficult to analyze features of the respectively received signals relative to each other, because there is an uncertainty as to whether any differences in the respectively received signals which are identified are truly indicative of a particular type of cardiac activity, or instead arise due to changes in the signal as it moves along its propagation path.

This is particularly true with regard to a conventional lead with a unipolar configuration, wherein the cardiac lead has an electrode at its distal tip, and whereby the stimulator housing, or a portion thereof, is used as the indifferent or return electrode. Clearly the spacing between the distal tip of the cardiac lead and the stimulator housing is many times larger than the size of the propagating wavefront. Even in the case of a conventional bipolar configuration, wherein a single lead carries an electrode at its distal tip, and another electrode, such as a ring electrode, disposed slightly behind the distal tip electrode, the spacing between the tip electrode and the ring electrode will still be larger than the propagating wavefront.

An electrode lead for a cardiac pacemaker is disclosed in U.S. Pat. No. 5,306,292 which has a distal tip with a number of closely spaced electrodes thereon, with the remainder of the hemispherical surface of the distal tip of the electrode being non-conducting. Circuitry in the pacemaker housing, connected to the respective electrodes via the electrode lead cable, allows the total conductive area and geometry of the distal tip of the cardiac lead to be selectively varied, by activating the electrodes in different combinations. For example, the combination of electrodes (i.e. conductive surfaces) at the tip of the cardiac lead which provides the lowest stimulation threshold can be determined by an auto-capture unit, so that energy consumption can be reduced.

Premature atrial contraction (PAC) is not an uncommon occurrence and, by itself, usually is not a cause for immediate concern, although its presence over an extended period of time may be an indication that the patient is a likely candidate for atrial tachyarrhythmias in the future.

A premature atrial beat generates a premature P-wave, which may or may not be conducted to the ventricles. The premature P-wave is often difficult to locate when it is superimposed on the preceding T-wave. If the premature P-wave is conducted to the ventricles, this usually occurs with a QRST configuration that is almost identical to the surrounding normal sinus beats. Some premature P-waves conducted to the ventricles, may closely simulate ventricular premature beats.

An IEGM which contains a P-wave originating from a premature atrial contraction which is not recognized as such, may be mis-diagnosed, which may in turn result in erroneous treatment.

It is therefore not only important to be able to reliably detect the presence of a PAC, but also to identify its source of origin, i.e., whether it arises from the left atrium or the right atrium.

SUMMARY OF THE INVENTION

It is an object of the present invention to provide a method and an apparatus which allow reliable identification of a premature atrial contraction.

It is a further object of the present invention to provide such a method and apparatus which additionally allow identification of the general location of the origination of a premature atrial contraction.

The above object is achieved in accordance with the principles of the present invention in a method and an apparatus employing a cardiac lead having a multi-electrode tip, wherein the electrodes are separated from each other but are spaced closely enough relative to each other so that respective unipolar electrical signals obtained from the different electrodes arise from the same propagating wavefront, and wherein these respective unipolar electrical signals are analyzed in terms of relative time offset and/or signal morphology in order to identify a premature atrial contraction.

As used herein, the term "unipolar" does not necessarily mean a signal referenced to the pacemaker housing, but means a signal referenced to a designated reference point, which is the same (i.e., is used in common) for all of the unipolar signals.

Because of their close spacing relative to each other, the individual electrodes (dots) on the distal tip of the cardiac lead will "see" the same wavefront, but that wavefront will arrive at different dots at slightly different times, so that the respective unipolar signals obtained from each electrode dot will be slightly shifted in time relative to each other. If the wavefront (i.e., the depolarization wave) arrives from the right, for example, the unipolar signal from the electrode dot at a right side of the distal tip will arrive at a detector connected to the lead in advance of the unipolar signal from the electrode dot at the left side of the distal tip. If the depolarization proceeds from the left, the opposite will occur. If the depolarization arrives in a direction substantially along the longitudinal axis of the distal tip (either from in front or behind the distal tip), all of the electrode dots will see the polarization at the same time, and there will be little, if any, time offset in the respective unipolar signals.

The respective unipolar signals which arise upon the occurrence of normal sinus activity (i.e., without any PAC), can be identified in advance, and deviations from this normal set of signals can then be determined and ascertained as representing an occurrence of a PAC. Moreover, such deviations from the normal signals can be classified as representing a PAC generated in the left atrium, as distinguished from a PAC generated in the right atrium.

The time differences (offsets) between the signals from respective pairs of electrode dots can be identified in several ways. In one embodiment the time offset, is found by identifying features of the different signals. The direction of the wavefront is calculated using simple trigonometric formulas, and the beat is classified based on this direction and on morphological information in the signals representing the beat.

In another embodiment, the components of the unipolar signals representing the depolarization in question are correlated with each other to identify different delays. This processing is undertaken retroactively, i.e., not in real time so that the signals can be correlated for a number of different delays. The more closely that two signals resemble each other, the higher their correlation. The highest correlation will be obtained for the delay representing the time it takes for the depolarization wavefront to proceed from one electrode to the next.

DESCRIPTION OF THE DRAWINGS

FIG. 1 is an end view (without the fixing elements) of the distal tip of a cardiac lead of the type used in the inventive method and apparatus, having a number of electrode dots.

FIG. 2 is a side view of the distal tip of FIG. 1, also showing the fixing elements.

FIG. 3 is a flowchart of a first embodiment of the inventive method, which is also practiced by the inventive apparatus.

FIG. 4 is a flowchart of a second embodiment of the inventive method, also practiced by the inventive apparatus.

DESCRIPTION OF THE PREFERRED EMBODIMENTS

Figure 9:
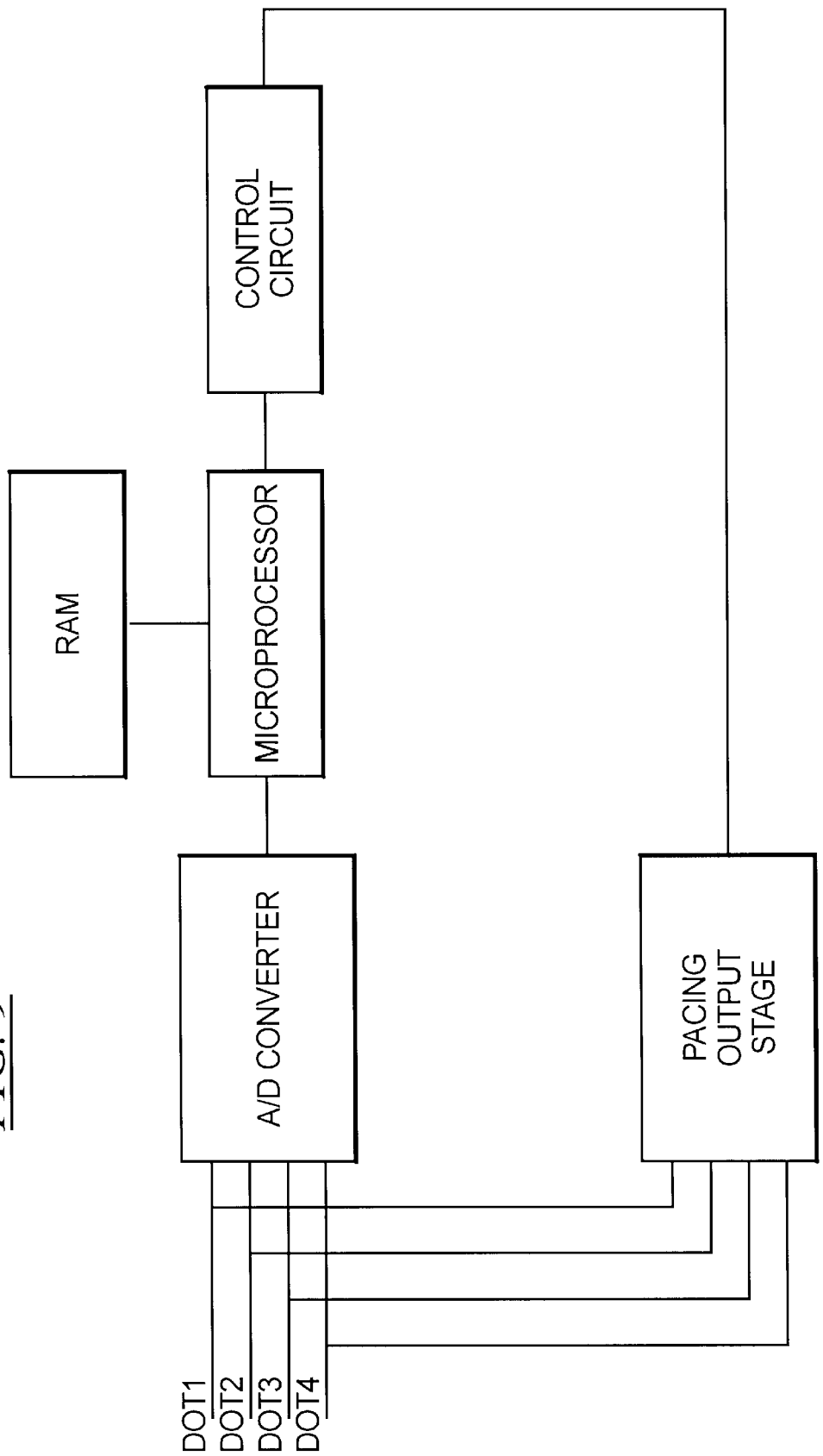
FIG. 9 is a schematic block diagram of an implantable cardiac therapy apparatus constructed and operating in accordance with the principles of the present invention.

FIGS. 1 and 2 show the distal end of a cardiac lead used in the method and apparatus of the invention. The cardiac lead 1 has a number of fixing elements 2 thereon, which are used to fix the distal tip of the lead 1 in the trabeculae of the heart in a known manner. The hemispherical end of the cardiac lead 1 has a number of electrodes thereon, in the form of dots. As is conventional, the exterior of the cardiac lead 1 is covered by insulating material, and therefore the electrodes 3 are separated from each other by this insulating material, which proceeds over the tip as well, each electrode 3 is composed of suitable electrically conductive material, and is connected to its own conductor (not shown) in the interior of the cardiac lead 1. These conductors proceed through the remainder of the lead 1 back to the proximal end thereof, which is electrically and mechanically connected to an implantable cardiac stimulator, the basic components of which are shown in FIG. 9. The internal circuitry of the cardiac stimulator is described in more detail in the aforementioned applications having Ser. No. 09/995,198 and Ser. No. 09/999,131.

Four electrodes 3 are shown in the exemplary embodiment of FIGS. 1 and 2, however, the inventive method and apparatus need only a minimum of three electrodes 3 in order to operate. Four is the preferred number of electrodes 3, however, more can be provided. The electrodes 3 must be simultaneously in contact with the myocardium.

The respective signals which are obtained from the electrodes 3 are unipolar signals.

Each electrode 3 preferably has a diameter of 0.5 mm, with the edge-to-edge distances between all of the respective electrodes 3 being approximately equal. A heart cell is about 0.02 mm wide and approximately 0.1 mm long. This means that one electrode 3 will cover a large number of heart cells. When a propagating wavefront due to polarization passes the multiple electrodes 3, the coupled heart cells are activated in sequence. This means that the signals registered by each electrode 3 in a unipolar fashion will "see" the identical pulse shape (waveform), but with small time offsets from electrode-to-electrode.

The detection circuitry in the cardiac stimulator will basically be formed by two stages, namely a conventional heart activity detector (QRS detector) which will detect the occurrence of a cardiac event, and a signal analysis stage which analyzes the detected unipolar signals to determine whether the detected event was due to a PAC.

The signal analysis can proceed in a number of different ways, however, all have in common the identification of a time difference between the signal from respective pairs of electrodes 3. Based on the assumption that the waveform morphology is identical along the short distances between the electrodes 3, the time delay between the signals from any pair of electrodes 3 can be determined. If one electrode 3 is arbitrarily selected as a reference, the analysis basically proceeds to identify when a signal at another of the electrodes 3 was received relative to the reception of the signal at the reference electrode 3. It should be noted that the identified time difference can be positive, indicating that the signal received at the other electrode followed the receipt of the signal at the selected reference electrode, or it could be negative indicating that the signal at the other electrode preceded the signal received at the selected reference electrode.

A simple embodiment, but also the most sensitive to noise, for identifying this time difference is to compare each of the incoming unipolar signals to a threshold and to mark the time when each of the unipolar signals exceeds that threshold. Based on the assumption that the respective morphologies of the two unipolar signals are identical, the unipolar signal which follows another unipolar signal will reach the threshold at a later time, and thus the respective times at which the threshold is exceeded in the unipolar signals from two of the electrodes 3 is an indication of the amount of time difference.

In another embodiment, the occurrence of a particular morphology feature, such as a peak value, can be identified in each unipolar signal, and the differences in the respective times at which these features occur in the two unipolar signals is then a measure of the time offset.

In a further embodiment, the similarity between the respective signals received from two of the electrodes 3 is determined, by an appropriate correlation algorithm. This technique is more computationally intensive, but also is more noise insensitive. The correlation can take place by shifting one of the unipolar signals in a shift register relative to the other signal, and after each step undertaking a bit-by-bit comparison. The number of shifts which is necessary to produce the highest degree of similarity indicates the time difference between the two signals.

As noted above, the time difference, and its magnitude, is an indication of the direction at which the wavefront arrived at the tip of the cardiac lead 1. A wavefront that arrives at a significant angle to the longitudinal axis of the cardiac lead 1 will produce a more pronounced difference between the respective signals registered by two of the electrodes 3, than will a wavefront which propagates substantially along the longitudinal axis.

A normal sinus signal can be assumed to occur along the longitudinal axis so that signals which arrive at a significantly different angle relative to the longitudinal axis can be assumed to represent a PAC. Alternatively, by using an external programmer with a display in telemetry communication with the implanted device, a physician can identify, by observing the time differences, the axis of propagation of a normal sinus signal for a given patient, and this can then be used as a reference so that any significant deviations therefrom will be identified as representing a PAC.

It should be noted that a PAC can usually be distinguished from other types of signals which may propagate along directions which deviate from the longitudinal axis, such as signals due to tachycardia or fibrillation. Signals due to tachycardia will be accompanied by an elevated heartbeat rate, which can be easily detected by known means. Signals occurring due to fibrillation will be chaotic and will arrive from multiple directions, which also can be easily ascertained. A signal representing a PAC will arrive at a direction which deviates from the direction of a normal sinus signal, but will do so relatively consistently, without elevation in the heartbeat rate, thereby making the identification as a PAC reliable.

These basic considerations are shown in the flowchart of FIG. 3, which represents a first embodiment of the inventive method. First, the depolarization direction is determined by one of the techniques described above using the time differences exhibited by respective unipolar signals from at least two of the electrodes 3. Next, a determination is made as to whether this depolarization direction is different from the direction normally expected for sinus activity. If the direction is determined to be different, the beat represented by the unipolar signals is classified as a PAC from the left atrium. If the direction is not different, the beat is classified as a normal P-wave.

In the embodiment of FIG. 4, the difference, if any, of the depolarization of an incoming set of signals is again determined, but the absence of a different direction (i.e., a "no" answer to the first inquiry) is not automatically classified as a normal P-wave. In the embodiment of FIG. 4, relevant morphological IEGM features are extracted from the current set of incoming unipolar signals, and a comparison is made, such as by comparing one or more of the signals to a stored template, to determine whether the features are similar to the features of a normal P-wave. If the result of this comparison indicates that the features are similar, then the beat is classified as a normal P-wave. If the features are determined to be dissimilar, the beat is classified as a PAC from the right atrium.

As shown in FIG. 9 for the exemplary embodiment of four dots (Dot 1 through Dot 4), but more dots can be used) the unipolar (IEGM) signal from each of the dots is supplied to an analog-to-digital (A/D) converter, wherein the signals are converted into digital form and are supplied to a microprocessor wherein they are analyzed as described elsewhere herein. For this purpose, the microprocessor has access to the contents of a RAM wherein the aforementioned template, or other reference information, can be stored. Dependent on the analysis, the microprocessor supplies a signal to a control circuit which, in turn, controls a pacing output stage to deliver therapy to the cardiac tissue via the electrode lead of FIGS. 1 and 2.

Figure 5:
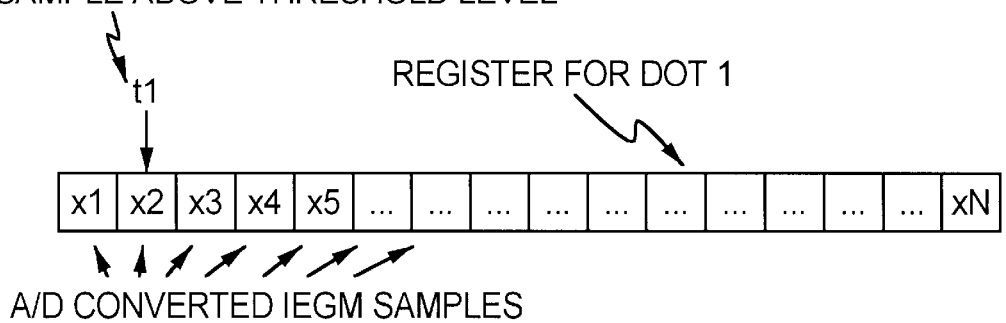
FIGS. 5, 6 and 7 respectively schematically illustrate the register contents for digitized samples of the unipolar signals respectively detected by different dots of the electrode of FIGS. 1 and 2, in accordance with the invention.
Figure 6:
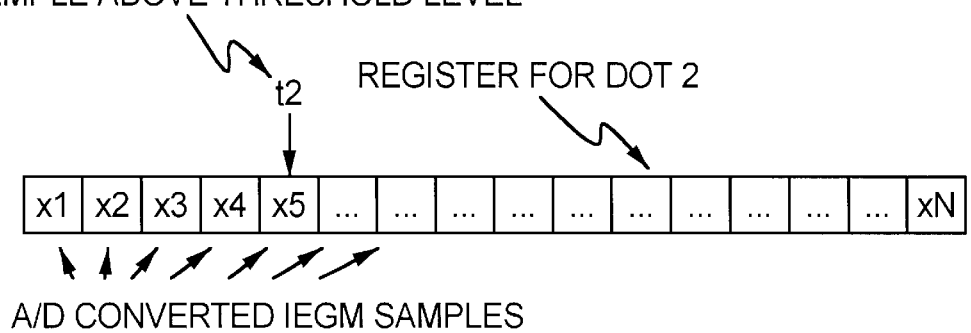
Figure 7:
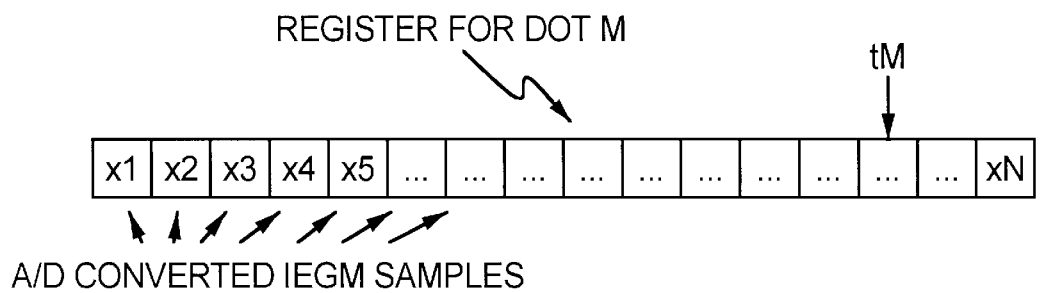

In one embodiment for conducting the analysis, the microprocessor can contain respective registers for the sampled signals from the different dots. Such registers are schematically shown in FIGS. 5, 6 and 7 for Dot 1 (FIG. 5), Dot 2 (FIG. 6) and Dot M (FIG. 7). Dot M is an arbitrary dot for explaining the principle of the analysis to indicate that the analysis is not limited to the exemplary embodiment of only four dots. Also, it should be noted that any of the Dots 3 shown in FIGS. 1 and 2 can be arbitrarily designated as Dot 1, with the remainder of the other dots then being sequentially designated.

As shown in FIG. 5, the register cells respectively contain one sample ($x_1$, $x_2$ ... $xN$) of the N samples of the digitized unipolar (IEGM) signal. Based on these stored samples, a designated feature is selected by or programmed into the microprocessor and its time of occurrence is identified, such as the first sample that is above a predetermined threshold. In FIG. 5, this occurs for sample x2, at a time t1.

The microprocessor analyzes the samples for Dot 2 in a similar manner, and finds that the same feature in those samples occurred in sample x5, at time t2. For the arbitrary further Dot M, it is assumed that this feature occurs at time tM.

Figure 8:
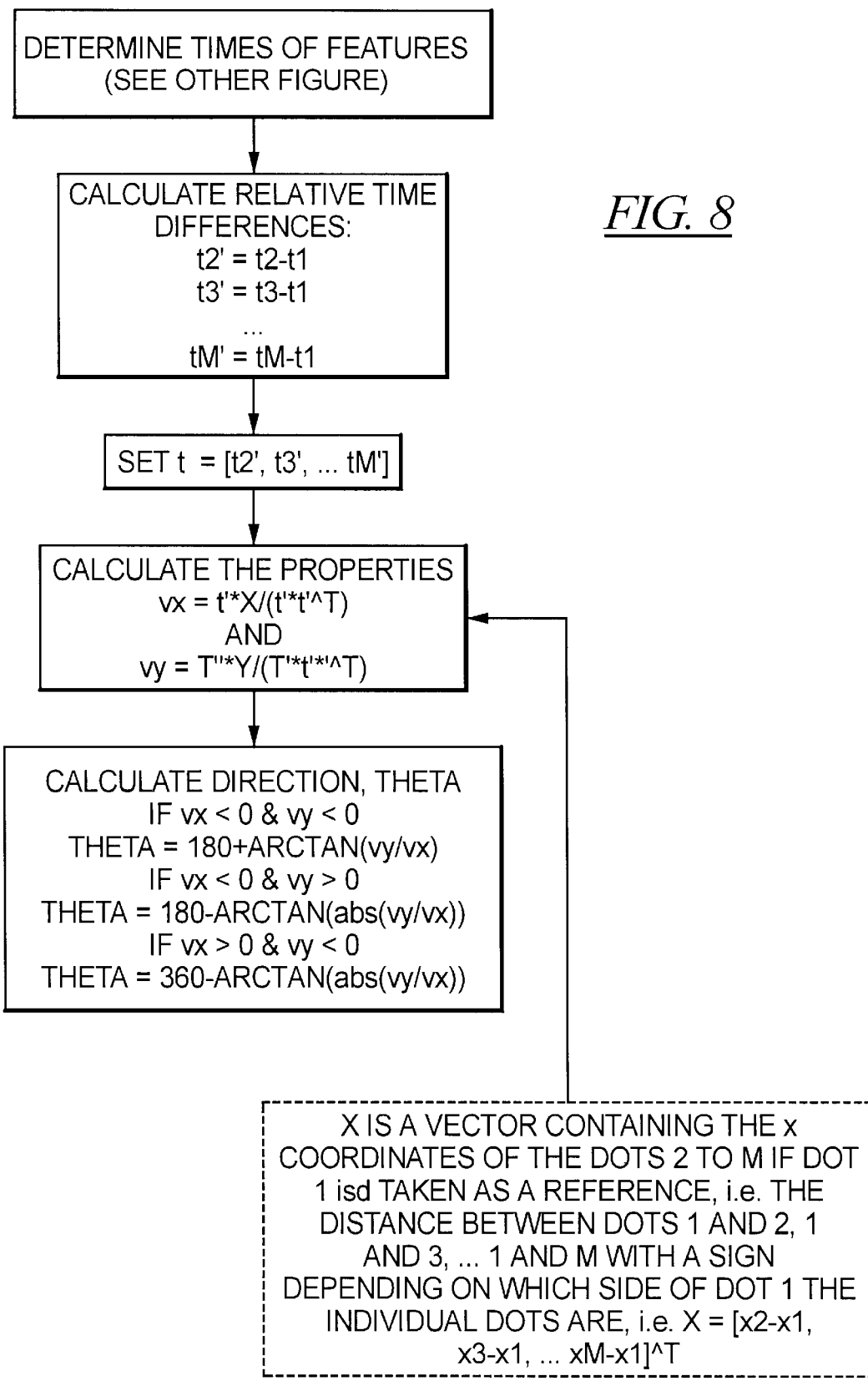
FIG. 8 is a flowchart for one embodiment for analyzing the unipolar signals to identify the direction of propagation of the wavefront represented by those signals.

The determination represented by FIGS. 5, 6 and 7 is included in the first block (determined times of features) in the algorithm shown in FIG. 8. After this initial time determination has been completed, relative time differences are calculated, such as t2'=t2−t1, t3'=t3−t1, ... ,tM'=tM−t1. Vectors Vx and Vy are then calculated according to the equations shown in FIG. 8, with t=[t2',t3', ... ,tM']. In the aforementioned formula, X and Y are vectors. X is a vector containing the x coordinates of the Dots 2 to M (if Dot 1 is used as a reference). These coordinates are the respective distances between Dots 1 and 2, Dots 1 and 3, ... Dots 1 and M, with a sign depending on which side of Dot 1 the individual dots are. Y is a vector generated in the same manner, using the Y coordinates of the Dots 2 to M.

In the next step, the direction of propagation of the incoming wavefront is calculated and designated as an angle theta from a reference direction, such as the longitudinal axis of the electrode lead. As shown in FIG. 8, if vx<0 and vy<0, theta=180° plus arctan (vy/vx). If vx<0 and vy>0, theta= 180−arctan ((ABS) vy/vx)). If vx>0 and vy<0, theta=360− arctan ((ABS) vy/vx)).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for identifying a premature atrial contraction, comprising the steps of:
   placing a cardiac lead having a tip with a plurality of electrodes thereon, electrically separated from each other, in contact with cardiac tissue so that at least two of said electrodes are simultaneously in contact with said cardiac tissue;
   obtaining respective unipolar signals from said at least two electrodes resulting from a depolarization wave in said cardiac tissue;
   analyzing said unipolar signals to identify a propagation direction of said depolarization wave relative to said tip of said cardiac lead; and
   classifying said depolarization wave as representing a premature atrial contraction dependent on said direction.

2. A method as claimed in claim 1 wherein said unipolar signals exhibit a time offset relative to each other, and wherein the step of analyzing said direction comprises analyzing said time offset to identify said direction.

3. A method as claimed in claim 2 wherein the step of analyzing said time offset comprises comparing each of said unipolar signals to a threshold and identifying respective times when the respective unipolar signals exceed said threshold, and identifying said time offset as a time between said respective times.

4. A method as claimed in claim 2 wherein the step of analyzing said time offset comprises identifying a selected feature in each of said unipolar signals, identifying respective times of reception of the respective identified features of the unipolar signals, and identifying said time offset as a time between said respective times of reception.

5. A method as claimed in claim 4 comprising employing a peak amplitude value of the respective unipolar signals as said identified feature.

6. A method as claimed in claim 2 wherein the step of analyzing said time offset comprises correlating the respective unipolar signals with each other while shifting one of said unipolar signals in time relative to the other unipolar signal, and identifying said time offset as an amount of shift of said one of said unipolar signals relative to the other of said unipolar signals which produces a highest correlation value.

7. A method as claimed in claim 1 wherein the step of placing the tip of a cardiac lead having a plurality of electrodes therein in contact with cardiac tissue comprises placing at least three electrodes on said tip simultaneously in contact with cardiac tissue.

8. A method as claimed in claim 7 comprising placing four electrodes on said tip simultaneously in contact with cardiac tissue.

9. A method as claimed in claim 1 comprising comparing said direction identified by analyzing said unipolar signals to a depolarization propagation direction associated with a normal sinus P-wave and, if said direction identified by analyzing said time offset significantly deviates from said direction associated with a normal sinus P-wave, classifying said depolarization wave as representing a premature atrial contraction from the left atrium.

10. A method as claimed in claim 9 comprising the step of, if said direction identified by analyzing said unipolar signals substantially coincides with said direction associated with a normal sinus P-wave, classifying said depolarization wave as originating from a normal sinus beat.

11. A method as claimed in claim 9 comprising the additional steps of, if said direction identified by analyzing said unipolar signals substantially coincides with said direction associated with a normal sinus P-wave, extracting at least one morphological feature from at least one of said unipolar signals, comparing the extracted feature to a feature known to be associated with a normal sinus P-wave, and if said features are similar, classifying said depolarization wave as originating from a normal sinus beat, and if said features are dissimilar classifying said depolarization wave as representing a premature atrial contraction from the right atrium.

12. An arrangement for identifying a premature atrial contraction, comprising the steps of:
   a cardiac lead having a tip with a plurality of electrodes thereon, electrically separated from each other adapted for placement, in contact with cardiac tissue so that at least two of said electrodes are simultaneously in contact with said cardiac tissue, to obtain respective unipolar signals from said at least two electrodes resulting from a depolarization wave in said cardiac tissue; and
   a signal processor supplied with said unipolar signals for analyzing said unipolar signals to identify a propagation direction of said depolarization wave relative to said tip of said cardiac lead and for classifying said depolarization wave as representing a premature atrial contraction dependent on said direction.

13. An arrangement as claimed in claim 12 wherein said unipolar signals exhibit a time offset relative to each other, and wherein said signal processor analyzes said direction comprises analyzing said time offset to identify said direction.

14. An arrangement as claimed in claim 13 wherein said signal processor analyzes said time offset by comparing each of said unipolar signals to a threshold and identifying respective times when the respective unipolar signals exceed said threshold, and identifying said time offset as a time between said respective times.

15. An arrangement as claimed in claim 13 wherein said signal processor analyzes said time offset by identifying a selected feature in each of said unipolar signals, identifying respective times of reception of the respective identified features of the unipolar signals, and identifying said time offset as a time between said respective times of reception.

16. An arrangement as claimed in claim 15 wherein said signal processor employs a peak amplitude value of the respective unipolar signals as said identified feature.

17. An arrangement as claimed in claim 13 wherein said signal processor analyzes said time offset by correlating the respective unipolar signals with each other while shifting one of said unipolar signals in time relative to the other unipolar signal, and identifying said time offset as an amount of shift of said one of said unipolar signals relative to the other of said unipolar signals which produces a highest correlation value.

18. An arrangement as claimed in claim 12 wherein said cardiac lead has at least three electrodes on said tip adapted for simultaneous placement in contact with cardiac tissue.

19. An arrangement as claimed in claim 12 wherein said cardiac lead has at least four electrodes on said tip adapted for simultaneous placement in contact with cardiac tissue.

20. An arrangement as claimed in claim 12 comprising a memory, accessible by said signal processor, in which a depolarization propagation direction associated with a normal sinus P-wave is stored, and wherein said signal processor compares said direction identified by analyzing said unipolar signals to said depolarization propagation direction associated with a normal sinus P-wave and, if said direction identified by analyzing said unipolar signals significantly deviates from said direction associated with a normal sinus P-wave, classifies said depolarization wave as representing a premature atrial contraction from the left atrium.

21. An arrangement as claimed in claim 20 wherein said signal processor, if said direction identified by analyzing said unipolar signals substantially coincides with said direction associated with a normal sinus P-wave, classifies said depolarization wave as originating from a normal sinus beat.

22. An arrangement as claimed in claim 20 wherein said signal processor, if said direction identified by analyzing said unipolar signals substantially coincides with said direction associated with a normal sinus P-wave, extracts at least one morphological feature from at least one of said unipolar signals, compares the extracted feature to a feature known to be associated with a normal sinus P-wave, and if said features are similar, classifies said depolarization wave as originating from a normal sinus beat, and if said features are dissimilar, classifies said depolarization wave as representing a premature atrial contraction from the right atrium.

23. An implantable cardiac stimulator for identifying a premature atrial contraction, comprising the steps of:
   a cardiac lead having a tip with a plurality of electrodes thereon, electrically separated from each other adapted for placement, in contact with cardiac tissue so that at least two of said electrodes are simultaneously in contact with said cardiac tissue, to obtain respective unipolar signals from said at least two electrodes resulting from a depolarization wave in said cardiac tissue;
   a signal processor supplied with said unipolar signals for analyzing said unipolar signals to identify a propagation direction of said depolarization wave relative to said tip of said cardiac lead and for classifying said depolarization wave as representing a premature atrial contraction dependent on said direction, and for generating an output signal indicating said direction; and
   a cardiac therapy administration arrangement connected to said cardiac lead and to said signal processor for generating and administering, via said cardiac lead, stimulation therapy to said cardiac tissue dependent on said output signal from said signal processor.

24. An implantable cardiac stimulator as claimed in claim 23 wherein said unipolar signals exhibit a time offset relative to each other, and wherein said signal processor analyzes said direction comprises analyzing said time offset to identify said direction.

25. An implantable cardiac stimulator as claimed in claim 24 wherein said signal processor analyzes said time offset by comparing each of said unipolar signals to a threshold and identifying respective times when the respective unipolar signals exceed said threshold, and identifying said time offset as a time between said respective times.

26. An implantable cardiac stimulator as claimed in claim 24 wherein said signal processor analyzes said time offset by identifying a selected feature in each of said unipolar signals, identifying respective times of reception of the respective identified features of the unipolar signals, and identifying said time offset as a time between said respective times of reception.

27. An implantable cardiac stimulator as claimed in claim 26 wherein said signal processor employs a peak amplitude value of the respective unipolar signals as said identified feature.

28. An implantable cardiac stimulator as claimed in claim 24 wherein said signal processor analyzes said time offset by correlating the respective unipolar signals with each other while shifting one of said unipolar signals in time relative to the other unipolar signal, and identifying said time offset as an amount of shift of said one of said unipolar signals relative to the other of said unipolar signals which produces a highest correlation value.

29. An implantable cardiac stimulator as claimed in claim 23 wherein said cardiac lead has at least three electrodes on said tip adapted for simultaneous placement in contact with cardiac tissue.

30. An implantable cardiac stimulator as claimed in claim 23 wherein said cardiac lead has at least four electrodes on said tip adapted for simultaneous placement in contact with cardiac tissue.

31. An implantable cardiac stimulator as claimed in claim 23 comprising a memory, accessible by said signal processor, in which a depolarization propagation direction associated with a normal sinus P-wave is stored, and wherein said signal processor compares said direction identified by analyzing said unipolar signals to said depolarization propagation direction associated with a normal sinus P-wave and, if said direction identified by analyzing said unipolar signals significantly deviates from said direction associated with a normal sinus P-wave, classifies said depolarization wave as representing a premature atrial contraction from the left atrium.

32. An implantable cardiac stimulator as claimed in claim 31 wherein said signal processor, if said direction identified by analyzing said unipolar signals substantially coincides with said direction associated with a normal sinus P-wave, classifies said depolarization wave as originating from a normal sinus beat.

33. An implantable cardiac stimulator as claimed in claim 31 wherein said signal processor, if said direction identified by analyzing said unipolar signals substantially coincides with said direction associated with a normal sinus P-wave, extracts at least one morphological feature from at least one of said unipolar signals, compares the extracted feature to a feature known to be associated with a normal sinus P-wave, and if said features are similar, classifies said depolarization wave as originating from a normal sinus beat, and if said features are dissimilar, classifies said depolarization wave as representing a premature atrial contraction from the right atrium.

* * * * *